US005539084A

United States Patent [19]

Geysen

[11] Patent Number: 5,539,084

[45] Date of Patent: Jul. 23, 1996

[54] METHOD FOR THE USE AND SYNTHESIS OF PEPTIDES

[75] Inventor: Hendrik M. Geysen, Menzies Creek, Australia

[73] Assignee: Coselco Mimotopes Pty. Ltd., Victoria, Australia

[21] Appl. No.: 752,437

[22] PCT Filed: Feb. 16, 1990

[86] PCT No.: PCT/AU90/00062

§ 371 Date: Sep. 6, 1991

§ 102(e) Date: Sep. 6, 1991

[87] PCT Pub. No.: WO90/09395

PCT Pub. Date: Aug. 23, 1990

[30] Foreign Application Priority Data

Feb. 17, 1989 [AU] Australia .............................. PJ2788/89

[51] Int. Cl.$^6$ ...................................................... A61K 38/02

[52] U.S. Cl. .......................... 530/334; 530/333; 530/336; 530/337; 530/332

[58] Field of Search .................................... 530/317, 332, 530/334; 525/54.11

[56] References Cited

PUBLICATIONS

Merrifield, Angew. Chem. vol. 24 No. 10 (Oct. 1985) 799–810.

Schoofs et al. J. Immun. vol. 140, 611–616 No. 2 (Jan. 1988) 611–616.

Chou et al. JACS vol. 93 Jan. 13 1971 267–268.

*Primary Examiner*—Jill Warden

*Assistant Examiner*—David Lukton

*Attorney, Agent, or Firm*—Sughrue, Mion, Zinn, Macpeak & Seas

[57] ABSTRACT

A method for the separation of at least one specific binding entity from a mixture of binding entities, which comprises the steps of contacting said mixture of binding entities with an immobilized peptide in which said peptide specifically binds to said specific binding entity, and separating the immoblized peptide/specific binding entity complex from the mixture of binding entities; an immobilized peptide-solid support preparation comprising a cleavable link between the peptide and the solid support, and a method for the preparation of a peptide from an immobilized peptide-solid support preparation.

9 Claims, 12 Drawing Sheets

(1) (2) (3) (4)

METHOD FOR THE USE AND SYNTHESIS OF PEPTIDES

This invention relates to the use of synthetic peptides in the separation of complex mixtures of binding entities, and to the synthesis of peptides.

In International Patent Application PCT/AU84/00039 there is disclosed a method for the simultaneous synthesis of large numbers of peptides. This method is based on the solid phase synthesis of peptides onto polyethylene rods or pins as solid supports. In that patent application, it is pointed out that the technique would be useful for systematically determining the continuous antigenic determinants of various antigens by synthesizing all of the overlapping peptides which could be made from the sequence of the antigen and then testing for the ability of the peptide to bind to a binding entity such as an antibody. In effect, there is disclosed a method for a systematic and very rapid determination of the continuous B cell epitopes of an antigen.

Subsequent research using this method has led to fur%her developments which enhance the usefulness of peptides synthesized on inert rods or similar supports. Theses further developments relate to modifications to the earlier invention which extend its use in systematic studies in the field of immunology. Basically the modifications of the earlier invention allow for two different end results: elution of the binding entity from the peptide/solid support complex and harvesting of the peptide from the solid support.

BRIEF DESCRIPTION OF THE DRAWINGS

In FIG. 1(*a*), the peptide is bonded to the epsilon-amino group of the lysine and the carboxyl of the proline is bonded to the solid phase support; cyclization between the alpha-amino group of the lysine and the ester moiety of proline liberates a peptide bearing an N-(delta-diketopiperazinyl-butyl)amido moiety. In FIG. 1(*b*), the site of attachment of the peptide and of the solid phase support is reversed; cyclization produces a peptide bearing an N-(omega-hydroxyalkyl)amido moiety.

FIGS. 2(*c*) and 2(*d*) illustrate the result of binding of the eluant from FIG. 2(*a*) with the SMV-N capsid protein and the WMMV-II capsid protein, respectively.

FIG. 3(*b*) illustrates the result of binding of the eluant from FIG. 3(*a*) with the JGMV capsid protein; FIGS. 3(*c*) and 3(*d*) illustrate the result of binding of the eluant from FIG. 3(*a*) with the SMV-N capsid protein and the WMMV-II capsid protein, respectively.

FIGS. 4(*c*) and 4(*d*) illustrate the result of binding of the eluant from FIG. 4(*a*) with the SMV-N capsid protein and the WMMV-II capsid protein respectively.

FIG. 9(*b*) illustrates the HLPC trace of a mixture resulting from methylamine induced cleavage of the peptide DNP-β-Ala-Pro-$NHCH_3$ bound to pins bearing a Pro-Lac linker moiety.

Figure 1B:
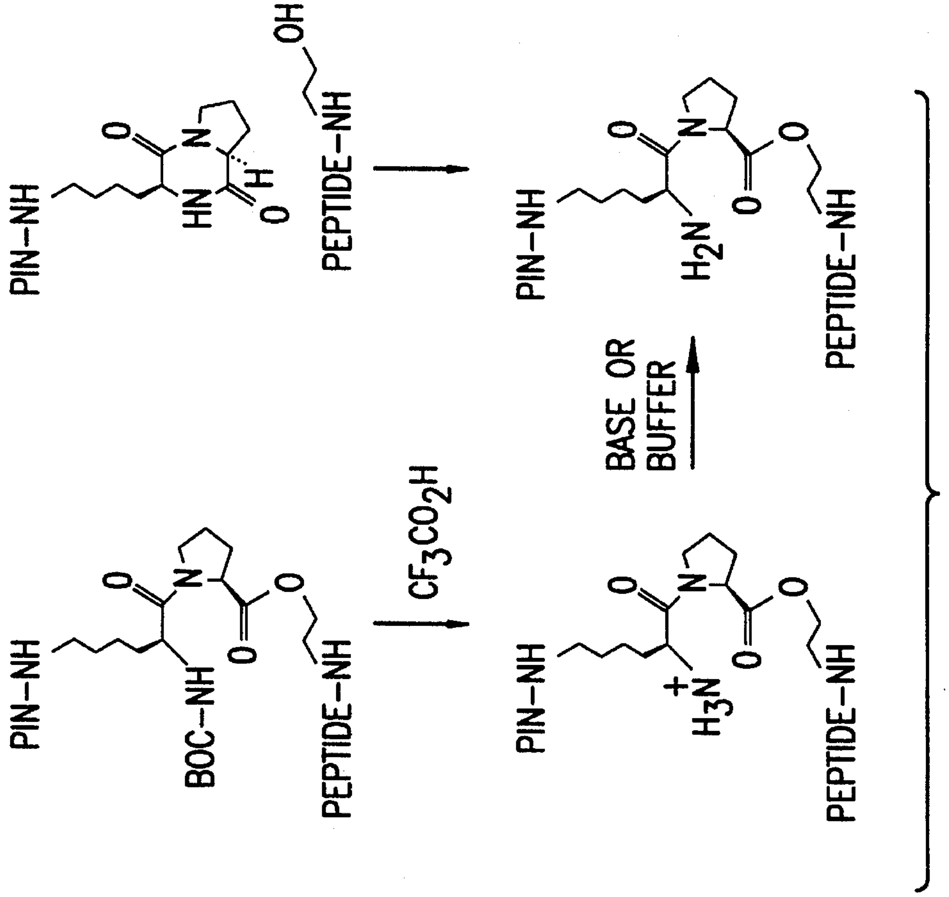
FIG. 1 illustrates the course of each of two reactions occuring as a result of two alternative points of attachment to a Lys-Pro linker moiety.

In general, the expression 'binding entity' as used throughout this specification means a macromolecule which binds specifically to another molecule. Examples of such 'binding entities' include antibodies reacting with the antigen which induced them; cellular receptors reacting with their ligand, eg., insulin receptors on cell surfaces binding insulin; and enzymes binding to their substrate. Equally, a binding entity can specifically react with an inhibiting molecule which prevents its normal function from being carried out; eg., enzyme inhibitors, antibiotics such as penicillin, and antagonists to cellular receptors. However, in this specification 'binding entity' generally has a more limited meaning and in this context implies the specific binding to a peptide or other molecule which was synthesized on the solid support or rod referred to above.

In a first aspect, the present invention relates to the separation of complex mixtures of binding entities into a large number of individual and highly specific binding entities. In the earlier patent applications antiserum was removed from a peptide-rod complex under conditions which destroyed the integrity of all reacting antibodies. This allowed the peptide-rod preparations to be used in further tests. The present invention is directed to a method for the removal, under milder conditions, of the binding entity which bound specifically to each of the peptides bound to rods or other solid supports. In this method, the integrity of the binding entities is maintained and they can be used for further tests.

In accordance with this first aspect of the present invention, there is provided a method for the separation of at least one specific binding entity from a mixture of binding entities, which comprises the steps of: (i) contacting said mixture of binding entities with an immobilized peptide in which said peptide specifically binds to said specific binding entity, and (ii) separating the immobilized peptide specific binding entity complex from the mixture of binding entities. If desired, the specific binding entity may then be recovered, for example by elution, or otherwise removed from the immobilized peptide specific binding entity complex.

Preferably, the immobilized peptide comprises a peptide-solid support preparation in which the peptide is immobilized on a solid support, such as a polyethylene rod or pin as previously described.

It will, of course, be appreciated that where more than one specific binding entity is to be separated from the mixture of binding entities, additional immobilized peptides are contacted with said mixture, with the peptides of these additional preparations specifically binding to the further specific binding entities to be separated.

The basic modification of the method of the earlier patent application is that after the peptide-rod complexes (for example in a 12×8 matrix) have been reacted with the particular binding entity of interest, they are thoroughly washed in phosphate buffered saline or some other suitable washing fluid. The peptide-rod binding entity complex can then be placed into an eluting solution which has been dispensed into microtitre plates. Thus each peptide-rod/binding entity complex is placed in elution solution completely separate from any other. In this way, each well of the microtitre plate will contain a solution of the binding entity which reacts specifically to a known peptide-rod complex. It will be appreciated that the harsher conditions described in the earlier patent application may, if desired, still be applied to the peptide-rod complex to ensure that all reacting binding entities have been removed, and so allow the peptide-rod complex to be used to study other binding entity preparations.

The elution solution used may be any of the formulations known to those skilled in the art. For example, solutions of high or low pH, solutions with high or low ionic strengths or solutions which combine these characteristics can be used to maximize the elution of the binding entities from the peptide-rod complex.

Alternatively, the synthesis of the peptides themselves can be modified to create peptides which allow the binding entity to be removed from the peptide-rod complex under more gentle conditions to minimize or avoid damage to or denaturing of the binding entity. An example of this would be to incorporate into the peptide, at the amino- or carboxy-terminus or both, a residue which changes one of its basic physico-chemical characteristics under well defined conditions. An example of such a residue is the amino acid histidine. This amino acid has a side chain which has a nitrogen atom which can accept a $H^-$ atom to form an imidazolium ion. The pK of this reaction is 6.00. Thus, any peptide which has had an additional histidine incorporated into it will alter its charge characteristics with a change in the PH between 7.0 and 5.0. At the higher pH it will be effectively neutral, at pH 5 it will have a positive charge. A change in pH will therefore fundamentally change affinity for the interaction between the binding entity and the rod coupled peptide. Thus a binding entity which bound to the peptide at a neutral pH (pH=7.0) would be expected to bind with much lower affinity at pH 5.0. In effect, altering the pH of the solution over a narrow range close to neutrality will 'lever' the binding entity away from the peptide to which it is bound. It must be appreciated that this example neither restricts the implementation of the method of the invention to the incorporation of histidine as the only residue which could be used, nor does it restrict the invention to the inclusion of residues which only change the electrostatic status of their sidechain with the pH of the solution in which they are placed.

Another modification of the synthesis method which can be used to successfully elute binding entities from a complex under mild conditions, involves synthesis of peptides of different lengths on the one rod. This can be conveniently done by modifying the coupling step in the synthesis procedure. Typically the number of active synthesis sites on a rod will be of the order of hundreds of nanomoles. For example, suppose that it was desired to synthesize the peptides of length from tetrapeptides to octapeptides in approximately equal quantities on each of the rods. One method by which this is achieved is as follows: The first four residues would be synthesized by the method described in International Patent Application PCT/AU84/00039. Subsequent couplings of residues to the growing peptide are performed with a mixture of the activated amino acid and a 'capping' agent which will prevent any amino group with which it reacts from taking any further part in subsequent synthesis cycles. In this example, for the coupling of the fifth amino acid (from the carboxy terminus) a mixture of the appropriate activated amino acid and coupling agent in the molar ratio of 4:1 would be used. This would ensure that about 20% of the synthesis sites would be 'capped' and that the peptides already synthesized on these particular sites would remain as tetrapeptides. A suitable 'capping' reagent would be acetic anhydride which would react with free amino groups to acetylate them. At the coupling step of the sixth synthesis cycle the molar ratio between activated amino acid and 'capping' agent would be increased to 3:1 to ensure that a further 20% of the synthesis sites were 'capped' and would remain as pentapeptides throughout the remaining synthesis cycles. During subsequent synthesis cycles the ratio of the appropriate activated amino acid and 'capping' agent is reduced to 2:1, 1:1 and in the final cycle, 1:0 (no 'capping' agent is required in the final cycle of the synthesis). The ratios in this example are obviously selected to ensure that 20% of the original synthesis sites are inactivated, so far as being able to participate in subsequent peptide extension cycles are concerned, in each cycle. In this manner, rods which have equal proportions of the tetra-, penta-, hexa-, hepta- and octapeptide versions of the parent octapeptide would be produced. The tetrapeptide version would be the carboxy terminus tetrapeptide of the octapeptide, the pentapeptide would be the carboxy terminus pentapeptide of the octapeptide and so on. It will be obvious that changing the concentration of the 'capping' solution at each stage of the synthesis procedure permits the proportion of each particular length of peptides to be varied at will. A particular binding entity will bind to different lengths of peptides with different affinities. Thus, a molecule which binds very tightly to a particular octapeptide will be eluted from a pentapeptide version of the same epitope under milder conditions which minimize any irreversible damage done to the binding entity. It will be appreciated that in this aspect the present invention extends to all methods which prevent subsequent addition of a residue to a peptide. It is not restricted to acetylation of the amino terminus of a peptide. It will be obvious that a residue which can force a conformational change in the peptide (described as a 'lever' residue above) can also be incorporated into the synthesis.

The solutions of binding entities which are produced by this first aspect of the present invention are effectively a fractionation of the original complex mixture of binding entities. Each one of these solutions represents the binding entities which react specifically to a known peptide. Each of the solutions is monospecific. Thus, the complex mixture of antibodies which represents an animal's polyclonal response to an antigen can be fractionated into solutions which are effectively monospecific. In this respect, these solutions behave like monoclonal antibodies. However, there are two major advantages which these preparations have over monoclonal antibodies. When preparing monoclonal antibodies, the epitope to which the monoclonal antibody responds is a matter of luck. In practice, a large number of clones have to be made and screened to obtain desired specificities. Monospecific antibody preparations made by the methods disclosed in this specification have their epitopes defined by the process itself. Secondly, monospecific antibody preparations can be made in accordance with the present invention from antisera from any species whereas, monoclonal antibodies are, in practice, limited mainly to murine antibodies.

The solutions of binding entities which are produced in accordance with this first aspect of the invention can be used in neutralization tests with viruses and toxins to directly determine which fractions are involved in the process of neutralization; they can be used in further binding studies to clearly indicate the relationships of the fractionating peptide an additional ligands. The fractions can be used in agglutination tests. Indeed, they can be used in any of the tests which are known to those skilled in the art to determine the regions of an antigen which are important in expression of a useful biological function, eg., the antigen inducing its antibody. The goal of being able to produce synthetic peptides for use in vaccines or as agonists and antagonists of receptors is greatly aided by the direct determination of the peptides which are specifically associated with particular biological functions as disclosed in this specification In a second aspect, the present invention relates to the synthesis of peptides, and in particular to methods for the cleavage of an immobilized peptide from a rod or pin or other solid support on which it has been synthesised. This is achieved by introducing a cleavable link into the peptide-solid support preparation between the support and the peptide. This link provides the site where cleavage will occur after the synthesis and the deprotection of sidechains of the peptides has been carried out. It will be appreciated that such special groups need to be selected with care. Many of the techniques developed for cleavage in conventional peptide synthesis will be unsuitable for use in this system. Either they are too dangerous to be used except by the most highly skilled technicians (an example is the traditional use of hydrogen fluoride as a cleavage agent) or they require extensive purification to remove unused reactant and byproducts of reaction, or both. Ideally the final peptide containing solutions should be able to be used directly in a variety of biological tests without purification and without any residual toxicity or containing any other component which might interfere in a test.

In accordance with this second aspect of the present invention, a cleavable link is added during the synthesis between the solid support and the the desired peptide, preferably between the solid support and the carboxy terminus of the peptide.

This aspect of the present invention includes the use of an ester link, a proline residue and a bifunctional amino acid residue as one such suitable cleavable link, and the chemistry to exploit this cleavable link takes advantage of a particularly vexatious problem in peptide synthesis. Basically, when proline is synthesized at the carboxy-terminus of a peptide being built up on a solid support, and another amino acid having a protected α-amino acid group is then synthesized to it, following the removal of the α-amino protecting group and neutralization, the proline will spontaneously cyclize to form diketopiperazine and cleave from the solid support. This reaction is illustrated in FIG. 1*a*.

Figure 1A:
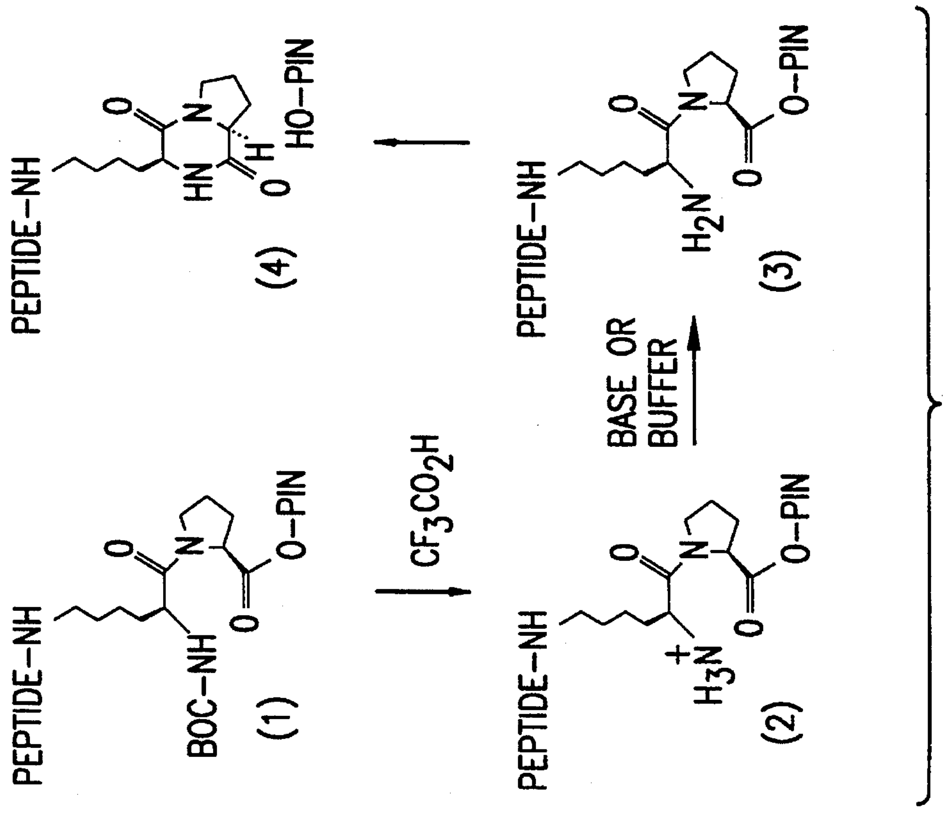
Figure 2A:
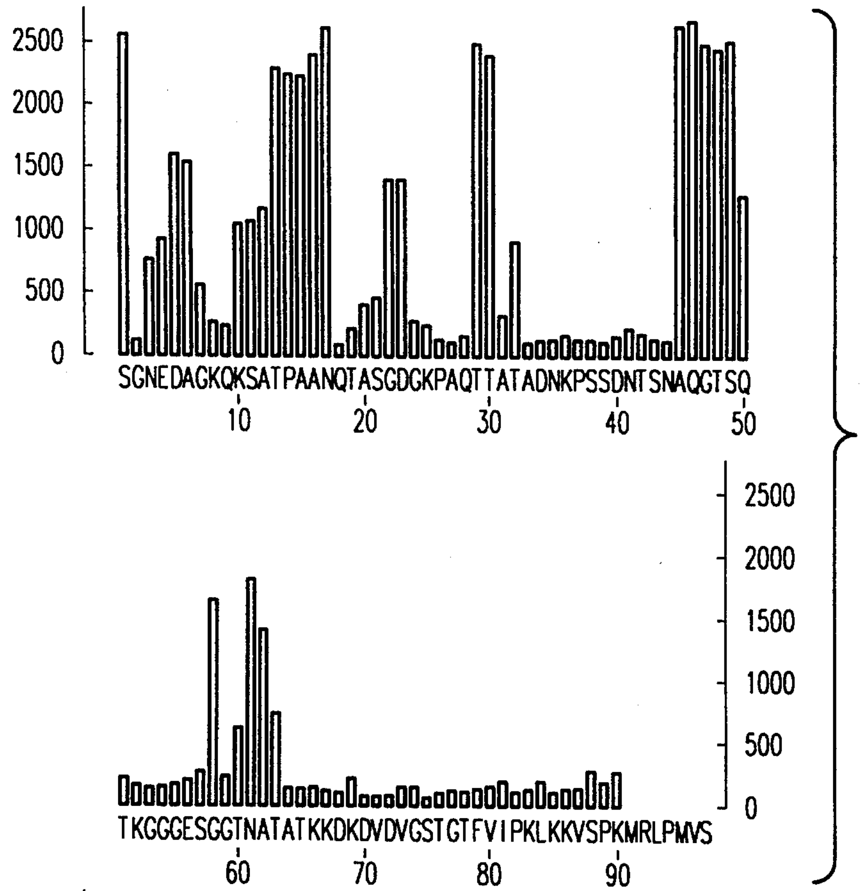
FIG. 2*a* illustrates the reaction (ELISA absorbance) between anti-JGMV serum and each of the possible octapeptides corresponding to residues 1–97 of JGMV capsid protein.
Figure 2B:
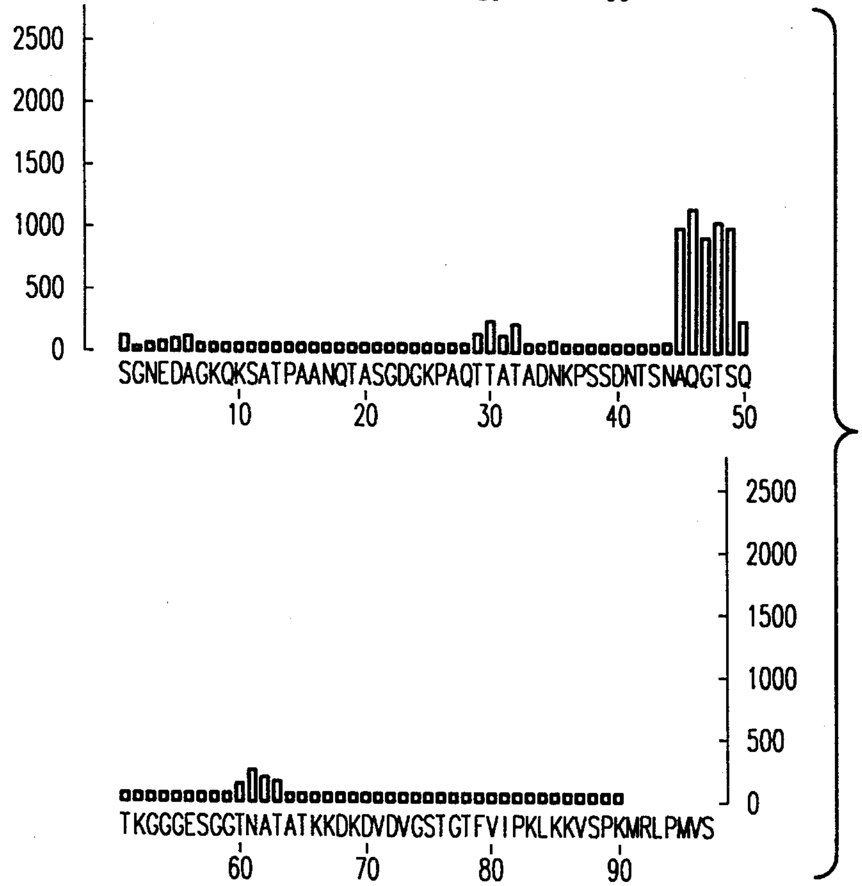
FIG. 2(*b*) illustrates the result of binding of the eluant from FIG. 2(*a*) with the JGMV capsid protein.
Figure 2C:
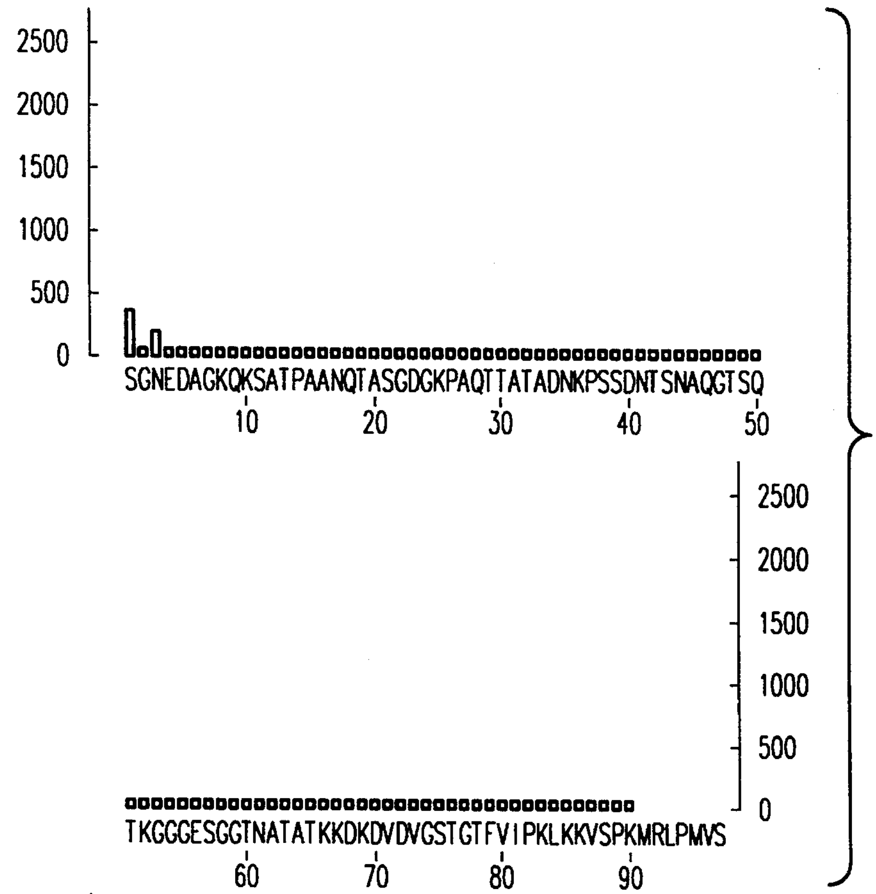
Figure 2D:
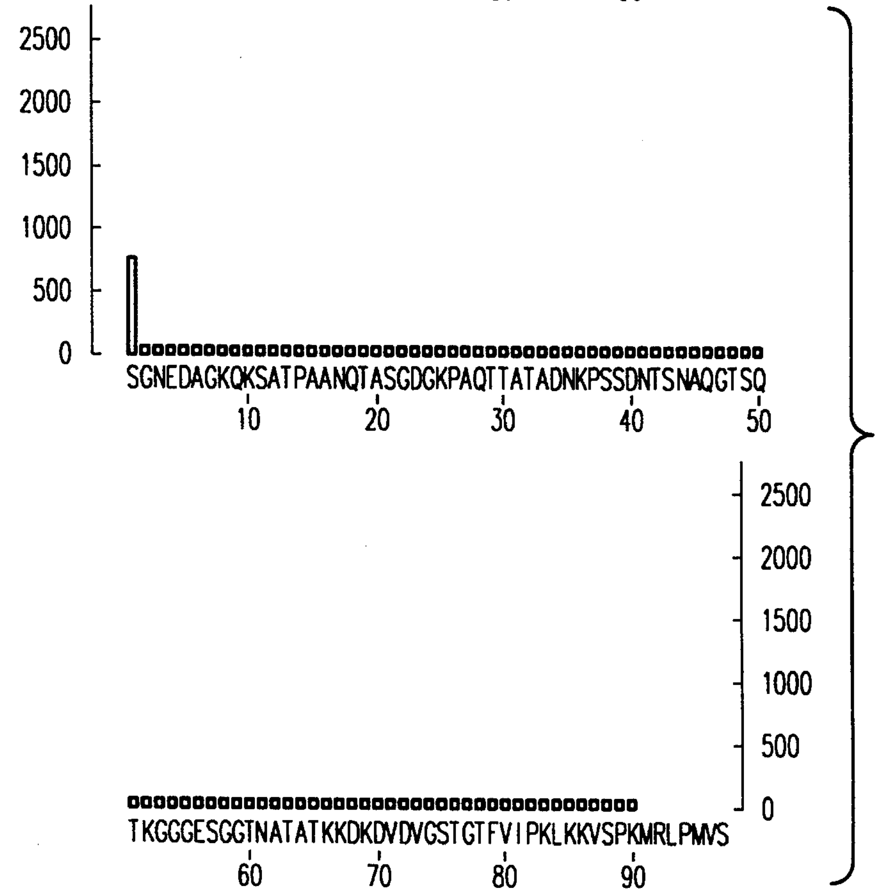
Figure 3A:
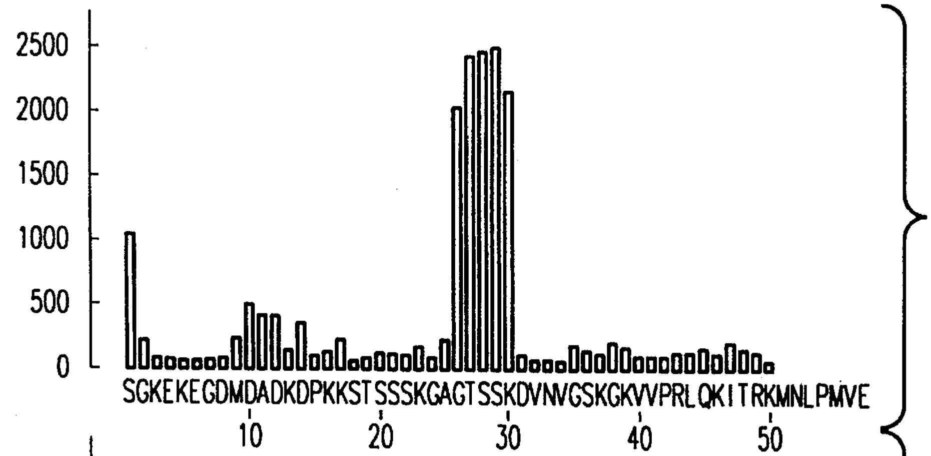
FIG. 3(*a*) illustrates the reaction (ELISA absorbance) between anti-SMV-N and each of the possible octapeptides corresponding to residues 1–57 of the SMV-N capsid protein.
Figure 3B:
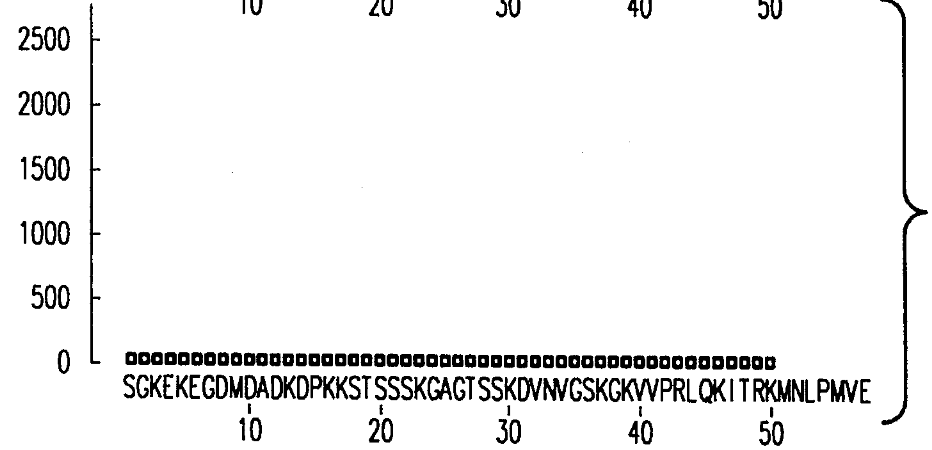
Figure 3C:
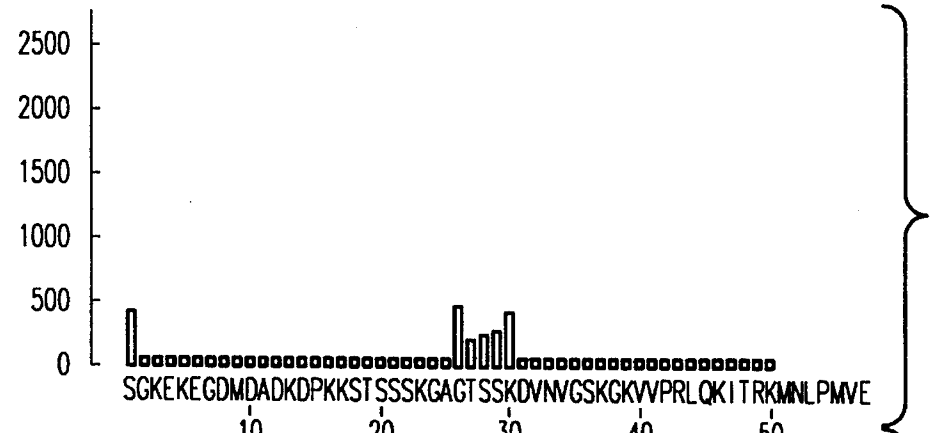
Figure 3D:
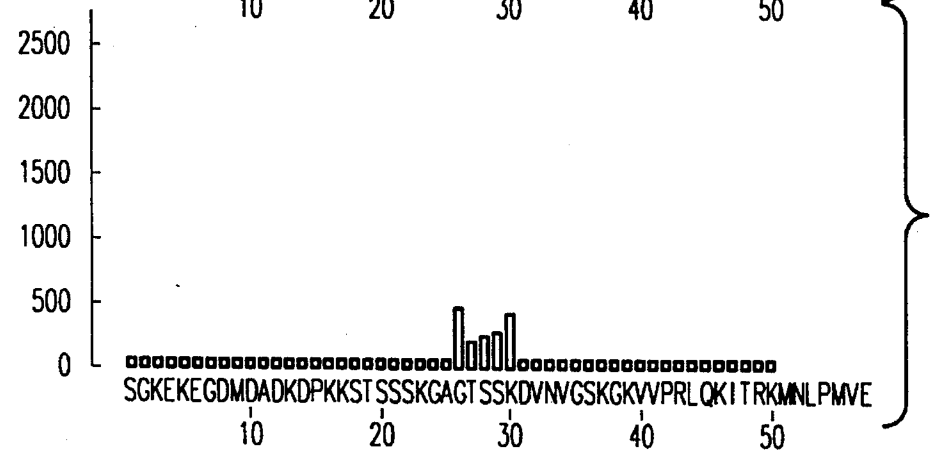
Figure 4A:
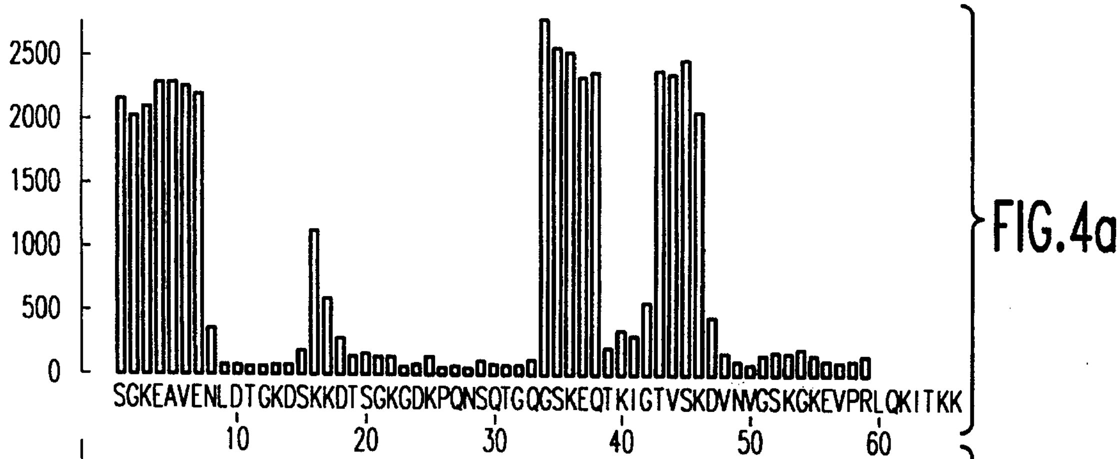
FIG. 4*a* illustrates the reaction (ELISA absorbance) between anti-WMMV-II and each of the possible octapeptides corresponding to residues 1–66 of the WMMV-II capsid protein.
Figure 4B:
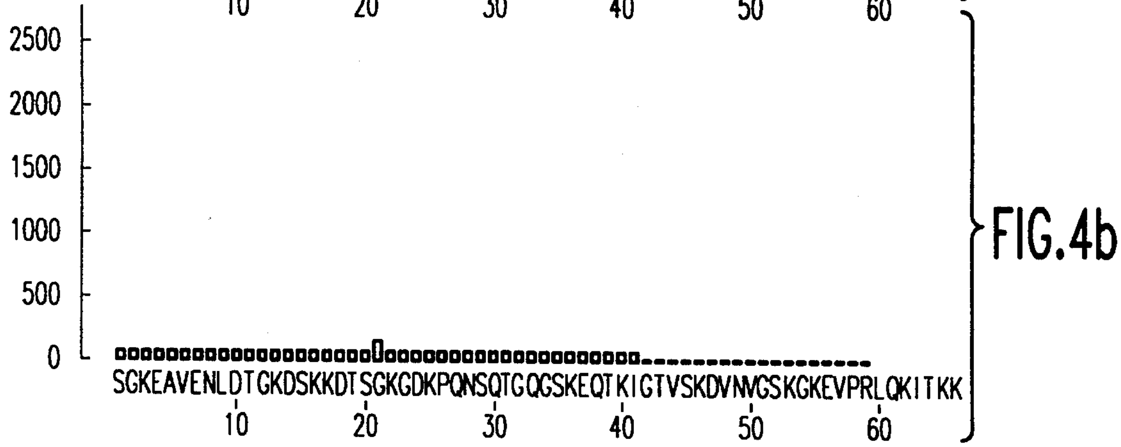
FIG. 4(*b*) illustrates the result of binding of the eluant from FIG. 4(*a*) with the JGMV capsid protein.
Figure 4C:
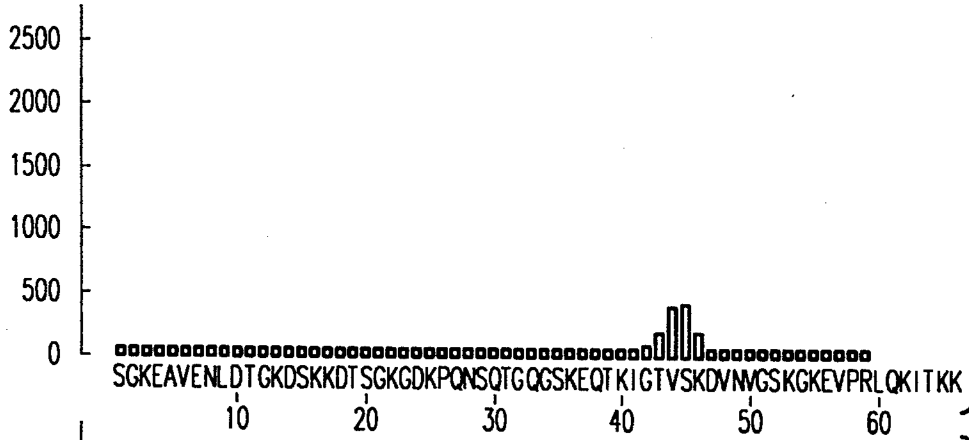
Figure 4D:
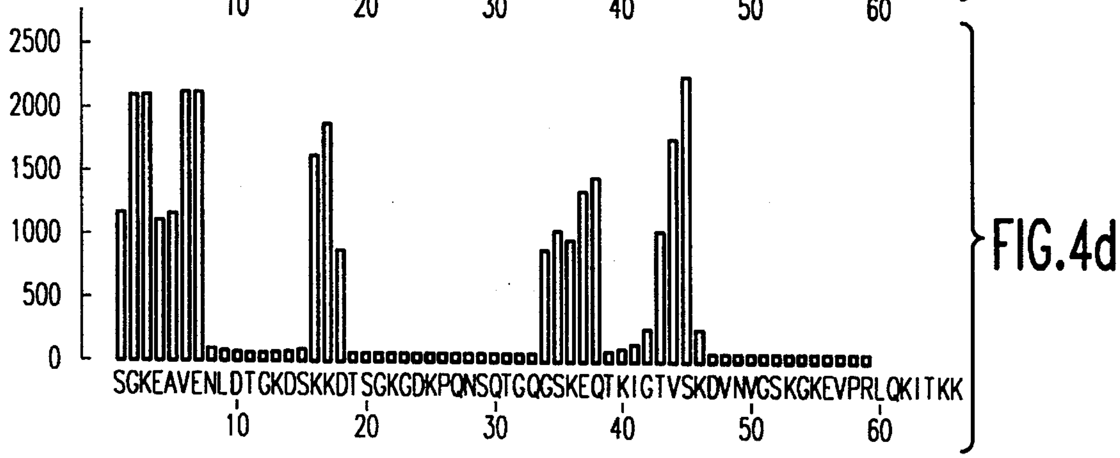
Figure 5A:
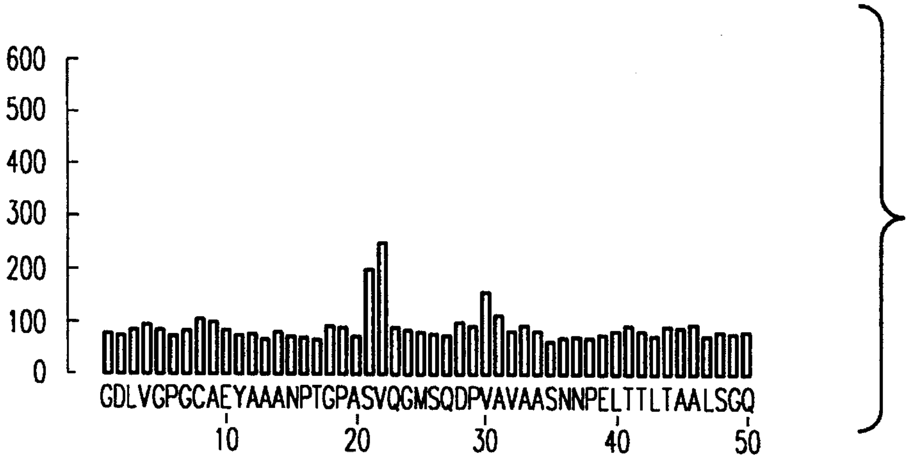
FIGS. 5(*a*), 5(*b*) and 5(*c*) illustrate the result of a T-cell proliferation assay resulting from exposure to each of the possible decapeptides corresponding to residues 1–161 of the MPB70 protein of M. Bovis BCG.
Figure 5B:
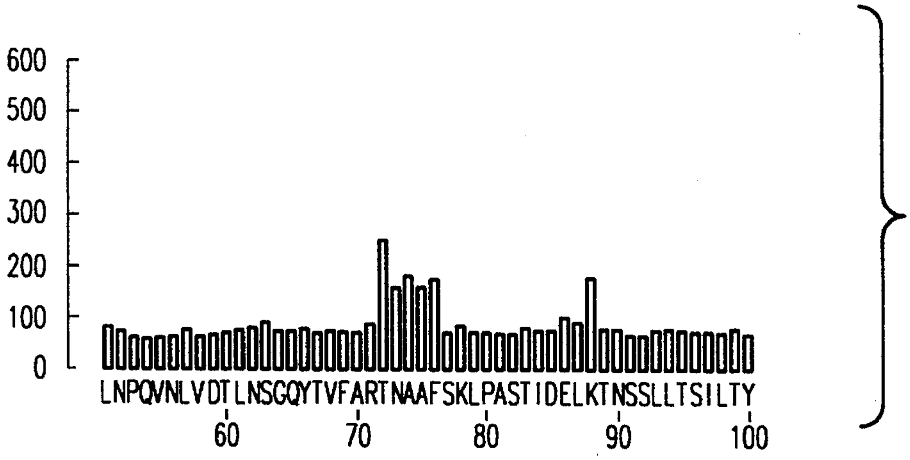
Figure 5C:
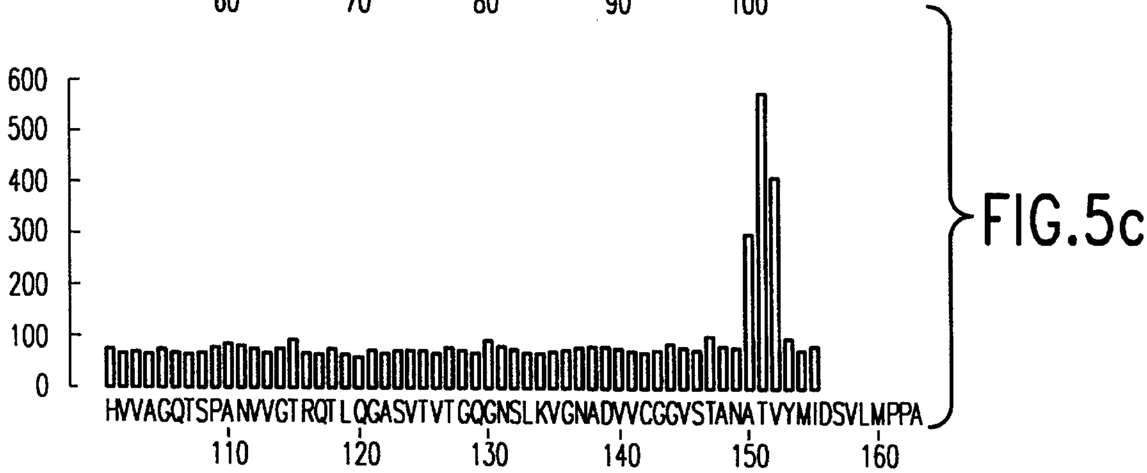
Figures 6A, 6B, 6C, 6D, 6E, 6F:
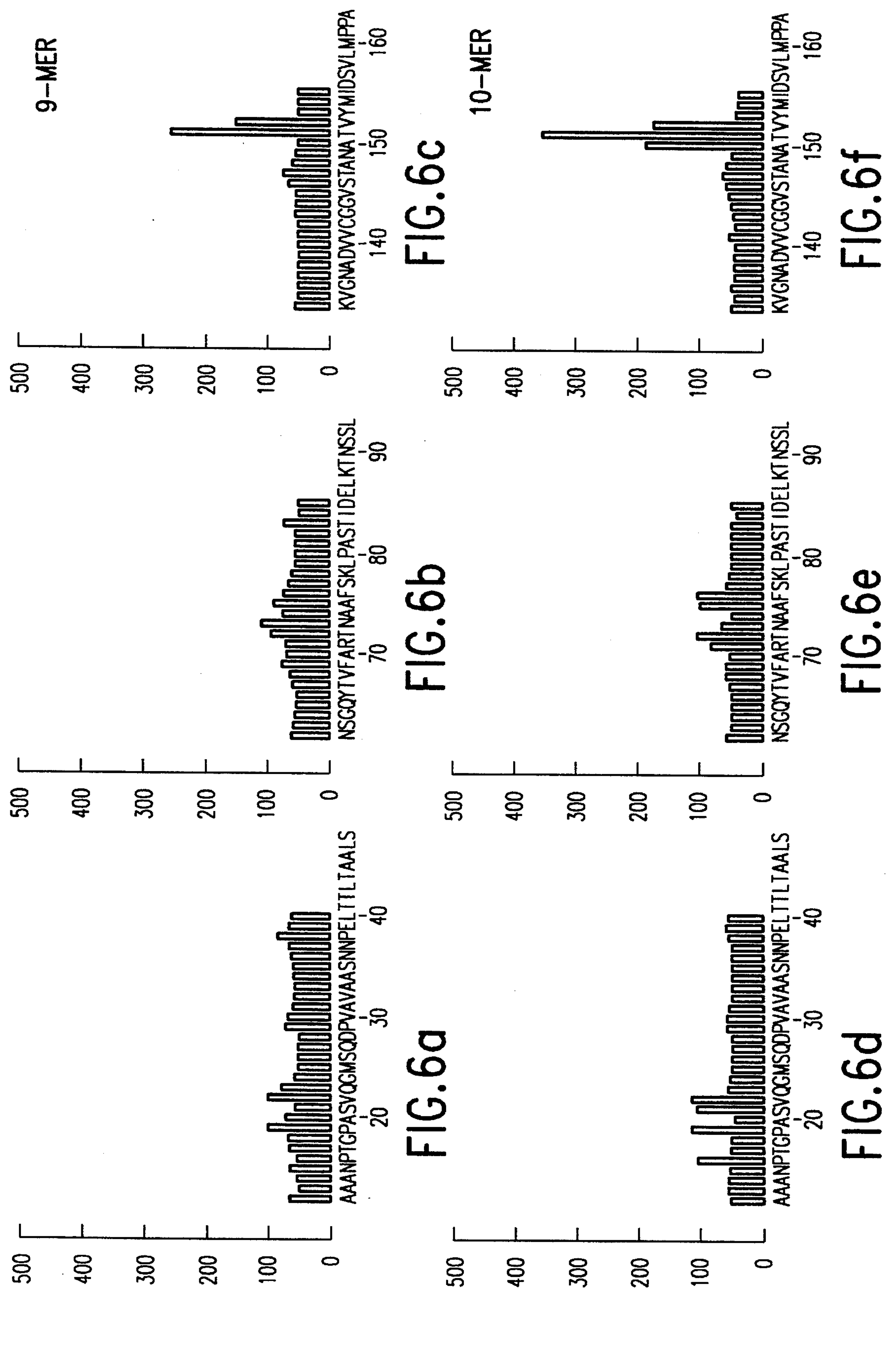
FIGS. 6(*a*), 6(*b*), 6(*c*), 6(*d*), 6(*e*), 6(*f*), 6(*g*), 6(*h*), 6(*i*), 6(*j*), 6(*k*) and 6(*l*) illustrate the results of T-cell proliferation by all possible 9-mers and 12-mers of the MPB70 sequence in the vicinity of residues 20–30, 72–85, and 150–161 of this peptide.
Figure 6I:
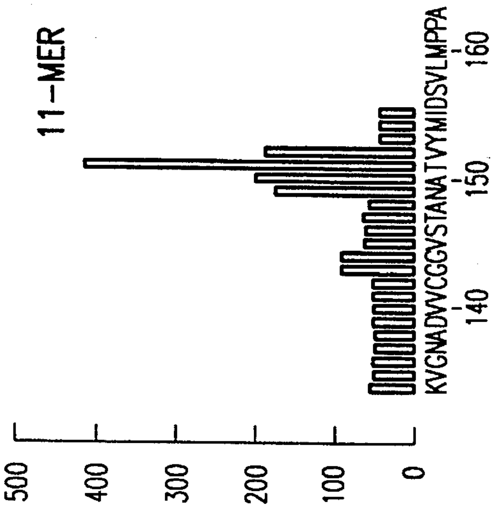
Figure 6H:
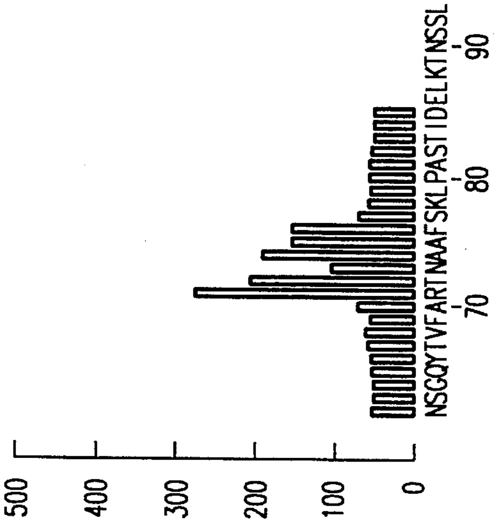
Figure 6G:
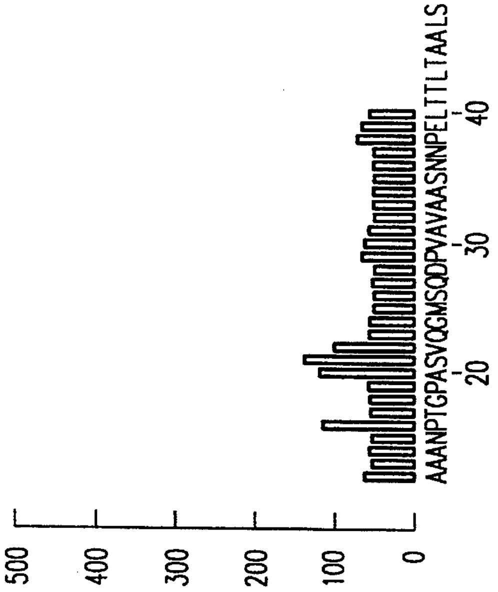
Figure 6L:
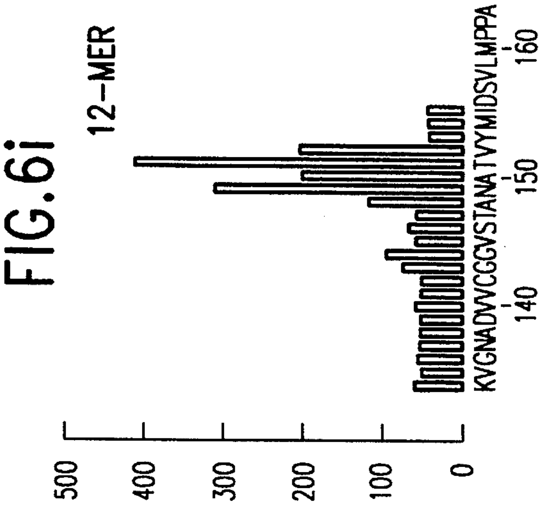
Figure 6K:
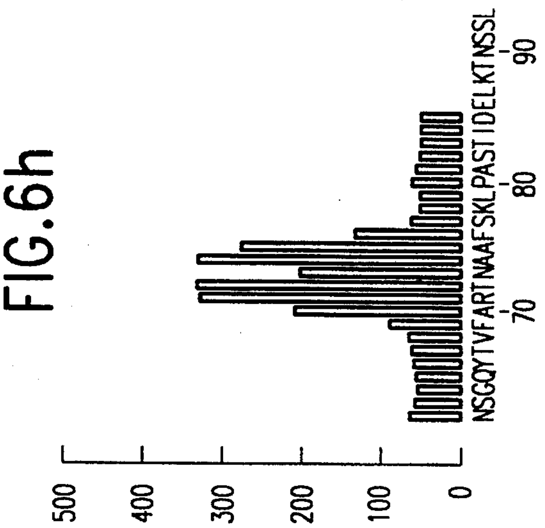
Figure 6J:
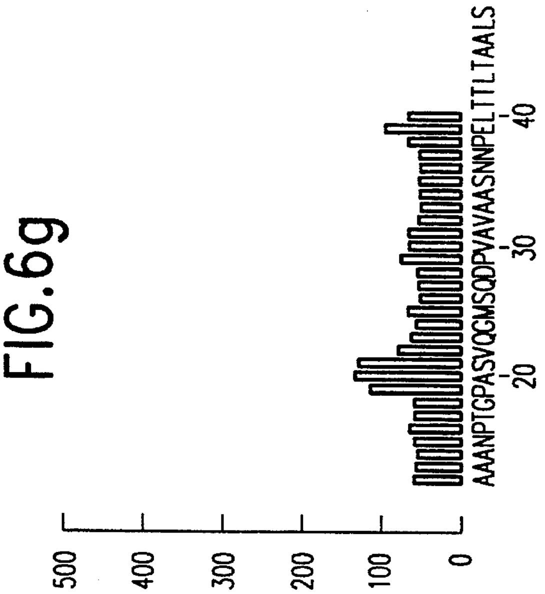

One embodiment of this aspect of the present invention takes advantage of the reaction illustrated in FIG. 1*a*, by initially adding proline to the solid support via an ester link. Where the solid support is a treated polyethylene rod or pin as disclosed in prior International Patent Application No. PCT/AU84/00039, the rod or pin preferably has spacer or linker residues, such as β-alanine or hexamethylene diamine residues, added before synthesis of the peptide thereon in accordance with the present invention. Then a bifunctional amino acid is added to the proline. An example of such a bifunctional amino acid which would be compatible with the chemistry of the Fmoc method of peptide synthesis is α-BOC, ε-Fmoc lysine, where BOC and Fmoc are the protecting groups t-butyloxycarbonyl and 9-fluorenyl-methyloxycarbonyl, respectively. A variation of this bifunctional amino acid which is compatible with the BOC chemistry of peptide synthesis is α-Z, ε-BOC lysine, where Z is the protecting group benzyloxycarbonyl. It will be noted that in both cases the usual protecting group, Fmoc and BOC respectively is protecting the ε-amino group rather than the α-amino group and furthermore the protecting group which normally protects the ε-amino group (BOC and Z, respectively) is now protecting the α-amino group. After addition of this amino acid the synthesis of the peptide proceeds in the usual manner. However, the peptide will now be attached to the ε-amino group of the lysine instead of the usual α-amino group. After deprotection of the sidechains, the α-amino group of the lysine next to the proline will be in the form of the $H_3N^-$ ion which can be neutralized under very mild basic conditions. When neutral the proline will spontaneously cyclize and cleave from the solid support as illustrated in FIG. 1*a*. This will leave the peptide in solution with the group —NH—$(CH_2)_4$-diketopiperazine attached at its carboxy terminus.

Suitable compounds which can be used to form the ester link between the proline residue and the spacer or linker residues on the solid support include, but are not restricted to, the following and their derivatives: N-acetyl serine, HO—$CH_2$—CH(NH.Ac)—COOH; glycolic acid, HO—$CH_2$—COOH; lactic acid, HO—CH($CH_3$)—COOH; and p-hydroxymethyl) benzoic acid, HO—$CH_2$—$C_6H_4$—COOH.

Alternatively, the bifunctional amino acid may be attached to the solid support (through the linker residues) before the proline. Again where the bifunctional amino acid is lysine the attachment is carried out through the ε-amino acid to allow the α-amino acid to take part in the cyclization step at the end of synthesis. This is then reacted with proline which has had its carboxy group esterified, for example with Fmoc ethanolamine or serine. The peptide synthesis is then carried out as usual. After side chain deprotection of the peptide, the α-amino group on the lysine attached directly to the solid support is gently neutralized and the proline moiety undergoes cyclization and cleavage of the peptide. In this variation, the diketopiperazine remains on the solid support and the peptide has a group derived from the esterifying group at its carboxy terminus, for example, the group —NH—$(CH_2)_2$—OH where the esterifying group is ethanolamine. The reaction is illustrated in FIG. 1*b*.

In some circumstances it may be undesirable to have the relatively large diketopiperazine moiety at the carboxy-terminal end of the cleaved peptide as shown in FIG. 1*a*. In another embodiment of this aspect of the invention, the cleavable link comprises an ester link between the carboxy group of the terminal amino acid and the linker residues on the solid support as described above. Suitable compounds for forming such an ester link have been described above. After synthesis of the desired peptide and side-chain deprotection, the peptide can be cleaved from the solid support at the ester link. For example, saponification with base will cleave peptide with a —COOH group at its carboxy terminus, and the resulting peptide solutions would simply need to be neutralized before biological testing could be carried out. An alternative cleavage method is to use methylamine in ethanol and/or water. This would result in cleaved peptides whose carboxy terminal group was —CO—NH—$CH_3$. This method has the advantage that the cleavage agent is volatile and would be removed from the peptide solution on lyophilization. The peptides could then be dissolved in any desired buffer for use in biological testing.

Those skilled in the art will appreciate that the cleavable link and the cleavage chemistry can be modified to yield different end groups as desired on the carboxy-terminal of the cleaved peptides.

Where polyethylene rods or pins as described in the International Patent Application referred to above are used as the solid support, the quantity of polypeptide synthesized on each rod or pin may be of the order of 100 nmole (about 0.07 mg for a hexapeptide). This amount is sufficient to carry out systematic studies in a large number of systems. These include, for example, studies of T-cell epitopes, hormone studies in which the peptides are used as agonists or antagonists of hormones, enzyme inhibition and tests for potential new antibiotics.

The peptides synthesised in accordance with this aspect of the invention can also be incorporated in other molecules. For instance, if cleavage is carried out in the presence of an activated carrier (such as keyhole limpet hamocyanin—a protein well known to those skilled in the art to induce excellent immunological responses in laboratory animals) then a set of antibody sera can be made by injecting the peptide-activated carrier protein preparations (with or without the use an adjuvant such as Freund's Adjuvant) into animals and subsequently collecting serum from them. In this way, a large number of antisera can be produced which can then be used in any of the usual immunological tests, eg., neutralization and binding assays. The same process can be used to combine the peptide with a monoclonal antibody. For instance, the step of conjugation of a peptide which mimics an epitope with a monoclonal antibody which specifically reacts with human erythrocytes (red blood corpuscles or hRBC) produces a modified monoclonal antibody which can be used as a diagnostic agent specifically for binding entities which react specifically with the epitope. In use in a diagnostic test, the patient's hRBC become coated with the peptide when mixed with the modified monoclonal antibody. If the patient has antibodies which bind to the epitope then his/her hRBC will clump together because the antibodies will bind with the peptide mimic of the epitope (this gives an indication of previous exposure to the epitope) which can be easily recognised by relatively untrained technicians. Obviously, the peptide combined with such a monoclonal antibody will be selected so that it is specific for a particular condition, eg., HIV-1 (human immuno-suppressant virus, type 1), or HBsAg (human Hepatitis B virus, surface antigen).

Further features of the present invention are illustrated, by way of example only, in the following Examples.

EXAMPLE 1

The amino terminal ends of the capsid protein of the potyvirus group of plant viruses have been shown to be specific to strains of these viruses. All of the overlapping octapeptides which could be made from the specific regions of the capsid protein were synthesized for three strains of potyviruses. The strains, and the sequences (using the single letter code for amino acids) on which the syntheses were based are:

Johnson grass mosaic virus (JGMV), residues 1 to 97:

| | | | | |
|---|---|---|---|---|
| 1 | SGNEDAGKQK | SATPAANQTA | SGDGKPAQTT | ATADNKPSSD |
| 41 | NTSNAQGTSQ | TKGGGESGGT | NATATKKDKD | VDVGSTGTFV |
| 81 | IPKLKKVSPK | MRLPMVS | | |

Soybean mosaic virus, strain N (SMV-N), residues 1 to 57:

| | | | | |
|---|---|---|---|---|
| 1 | SGKEKEGDMD | AKDKPKKSTS | SSKGAGTSSK | DVNVGSKGKV |
| 41 | VPRLQKITRK | MNLPMVE | | |

Watermelon mosaic virus strain 2 (WMMV2) residues 1 to 66:

| | | | | |
|---|---|---|---|---|
| 1 | SGKEAVENLD | TGKDSKKDTS | GKGDKPQNSQ | TGQGSKEQTK |
| 41 | IGTVSKDVNV | GSKGKEVPRL | QKITKK | |

Each series of octapeptides was synthesized and reacted with an antiserum which had been previously been shown to exhibit a degree of specificity for one of the strains of potyvirus. The antibodies were eluted under acidic conditions and each antibody fraction was tested for binding to capsid protein of the different strains of potyvirus. FIGS. 2, 3 and 4 represent the reaction with the specific region of the capsid protein of strains JGMV, SMV-N and WMMV2, respectively. In each of these figures, a) gives the absorbency in an ELISA test with the serum raised against the homologous strain; the other sub-figures summarise the reaction of the eluant (of the reaction between the peptides of the virus strain and the homologous antiserum) with the capsid protein of different strains—b) gives the result of binding of the eluent with JGMV capsid protein; c) gives the binding with SMV-N capsid protein; and d) gives the binding with WMMV2 capsid protein.

These results demonstrate that antibody preparations can be fractionated using the method of the present invention. It further illustrates that the antibody fractions, after elution, not only retain, but often increase, their specificity. Furthermore, they vividly explain the observation that while strain JGMV has little cross-reaction with either of the other two strains, there is some cross-reaction between SMV-N and WMMV2. In addition, the fractionation has led to the preparation of antisera to distinguish between the two cross-reacting strains of potyvirus because antiserum which reacts with the peptide $^{34}$GSKEQTKI (in the WMMV-II sequence) reacts strongly with WMMV-II capsid protein and has no binding to the SMV-N strain.

EXAMPLE 2

Sets of rods were synthesized with the following peptide: α-Z, ε-DNP lysyl-proline attached to serine spacers by the synthesis method described in detail in International Patent Application PCT/AU84/00039. DNP is the dinitrophenyl group and is a chromophore by which the rate of cleavage of the peptide could be measured. The rods were then exposed to 0.05% NaOH solution and the optical density measured at 405 nm. Results of this experiment are given in Table 1 and demonstrate that the peptide does cleave from the rods under relatively mild conditions, i.e. unbuffered 0.05% NaOH solution.

TABLE 1

RATE OF PEPTIDE CLEAVAGE

| | Optical density | | |
|---|---|---|---|
| Time | Mean | sd | % complete |
| 0 min | 0.064 | 0.002 | 0% |
| 5 min | 0.138 | 0.016 | 23% |
| 15 min | 0.284 | 0.007 | 47% |
| 30 min | 0.420 | 0.015 | 70% |
| 60 min | 0.569 | 0.079 | 95% |
| 90 min | 0.579 | na | 97% |
| 120 min | 0.600 | 0.046 | 100% |

The above results demonstrate that larger peptides synthesised on the rods with the lysyl-proline cleavage group can similarly be removed from the rods under relatively mild conditions.

EXAMPLE 3

All overlapping decapeptide sequences which could be made from the MPB70 protein of *Mycobacterium bovis* BCG were synthesized on rods with a cleavable link. This protein is a major component of BCG and is known to stimulate T-cells. Each peptide was cleaved from its rod and individually tested for its ability to cause proliferation in a T-cell preparation. This was measured by the production of gamma-interferon which is released when T-cells are stimulated. The sequence of the protein is:

| | | | | |
|---|---|---|---|---|
| 1 | GDLVGPGCAE | YAAANPTGPA | SVQGMSQDPV | AVAASNNPEL |
| 41 | TTLTAALSGQ | LNPQVNLVDT | LNSGQYTVFA | RTNAAFSKLP |
| 81 | ASTIDELKTN | SSLLTSILTY | HVVAGQTSPA | NVVGTRQTLQ |
| 121 | GASVTVTGQG | NSLKVGNADV | VCGGVSTANA | TVYMIDSVLM |
| 161 | PPA | | | |

The rods were grafted and BOC-hexamethylene diamine coupled to them using the methods described in International Patent Application PCT/AU84/0039. Then Fmoc-serine(t-butyl) is coupled to the rod using the usual Fmoc-chemistry. The serine was deprotected using piperidine/dimethyl formimide (DMF) to remove the Fmoc-group in the usual way. The α-amino group of the serine was then acetylated by standing in an acetic anhydride solution consisting of 40 ml triethylamine, 80 ml acetic anhydride in 200 ml DMF for 90 min. The rods were then washed three times in methanol and allowed to dry. The t-butyl group on the serine side chain was then removed with trifluoroacetic acid (TFA) for 50 mins allowed to dry in air and placed under vacuum. Then BOC-proline was coupled to the free —OH group of the serine. The symmetrical anhydride of proline was prepared. 3.48 g of BOC-proline-OH was added to 1.67 g of N,N'dicyclohexylcarbodiimide (DCC) in 100 ml of dichloromethane (DCM) and allowed to react for 20 min at room temperature. The material was filtered and evaporated to dryness. The residue was dissolved in 150 ml of DMF and just before contacting the rods, 1.5 g of dimethylaminopyridine (DMAP) and 157 mg DCC added to the solution. The rods were allowed to react for 24 hours to allow the esterification reaction to go to completion. They were then washed in methanol. α-BOC lysine (ε-Fmoc) was then coupled to the proline using the usual Fmoc chemistry. After coupling and washing, the Fmoc protecting group was removed from the ε-amino group of the lyeine in the usual way (piperidine in DMF). Then the amino acids of the peptides were coupled using the usual Emoc chemistry. After synthesis was completed, the sidechains were deprotected with a solution of TFA:phenol:ethanedithiol (95:2.5:2.5). The rods were then washed with TFA for 5 mins and given two washes in methanol for 1 min. They were then left to stand in phosphate buffered saline (pH 5.0) for 48 hours. Each rod was then allowed to stand in cleavage solution for 4 hours with occasional agitation. The cleavage solution was 0.08% NaOH, 0.01% phenol red (as an indicator) in deaerated distilled water. Each rod was placed in 150 μl dispensed into a polystyrene microtitre plate. The rods were then removed from the plates and 20 μl of phosphate buffered saline (pH 7.2) added to each well of the plate. The peptide solutions were stored frozen until used.

The results obtained in the T-cell proliferation test are illustrated in FIGS. *5a–5c*. Three regions in the sequence identified as significant stimulators of T cells were:

$^{20}$SVQGMSQDPVA $^{72}$TNAAFSKLPASTID $^{150}$ATVYMIDSVLMP

All peptides from length 9-mer to 12-mer of the MPB70 sequence around these regions were synthesized on rods and then cleaved in the same manner as described above. These peptide preparations were again tested for their ability to stimulate T-cell proliferation. The results are given in FIGS. *6a–6l*. These results demonstrate that T-cell proliferation can be reproducibly stimulated by peptides synthesized using this invention. It also illustrates that large numbers of peptides can be used in such tests to systematically study variants of the stimulatory peptide.

EXAMPLE 4

The test peptide VQAAIDYING, well known to those skilled in the art (corresponding to residues 65–74 of the acyl carrier protein of *Escherichia coli*), was synthesized on pins. A labile ester link was introduced by synthesising a separate compound, Fmoc-Pro-Lact-OH.

Triethylamine (7 ml, equivalent to 50 mmol) and 10 g of phenacyl bromide (=50 mmol) were added to a stirring solution of L-lactic acid (5.4 g of an 85% aqueous solution, equivalent to 50 mmol). After 40 h at room temperature, the reaction mixture was extracted with 100 ml of hot water. The organic phase was then sequentially washed with the following aqueous solutions: 10% citric acid, 7% sodium bicarbonate and finally with saturated NaCl solution (brine). The organic phase was then dried. Evaporation of the solvent yielded a gum which crystallized on standing. The solid was triturated with 50 ml of ether and collected by filtration. The 3.47 g yield of phenacyl lactate (Lac-OPa) was 68% of the theoretical for the step.

Fmoc-proline was then coupled to the phenacyl lactate. 2.06 g (10 mmol) of dicyclohexylcarbodiimide was added to a 4° C. solution of Fmoc-Pro-OH (3.37 g, 10 mmol), phenacyl lactate (2.08 g, 10 mmol) and dimethylaminopyridine (240 mg, 2 mmol) in 50 ml of dichloromethane. The reaction mixture was filtered after 22 h and the filtrate evaporated. The resulting gum was dissolved in 100 ml ethyl acetate and washed sequentially with the following aqueous solutions: 10% citric acid, twice in 4% sodium hydroxide, 10% citric acid and finally, brine. The organic solution was evaporated yielding the product as 4.36 g of a yellow gum. This material was used without further purification.

The Fmoc-Pro-Lac-OPa was then converted to the dicyclohexylamine (DCHA) salt. The crude product was dissolved in 30 ml of ethyl acetate and 100 ml of glacial acetic acid and 30 ml of water were added. 6 g of zinc was added to the solution and the suspension stirred for 16 h at room temperature and then filtered. The gum obtained upon evaporation of the filtrate was partitioned between 150 ml of ethyl acetate and 200 ml of water. The organic phase was sequentially washed with the following aqueous solutions: brine, 10% citric acid, brine. The pale yellow oil obtained after evaporation was dissolved in 50 ml of ether. A solution of 2.00 g dicyclohexylamine (11 mmol) in 50 ml of light petroleum ether (40°–60° C. fraction) was slowly added to the ether solution and a white precipitate formed which became crystalline on standing. This was collected by filtration and washed with 50 ml of ether three times and finally air dried. The yield of 4.46 g Fmoc-Pro-Lac-OH.DCHA obtained was 95% of the theoretical. This compound is stable and can be stored until required for use.

However, before covalently coupling to the pins, it must be converted to the free acid. Obviously, the amount used will depend of the number of pins to be coupled. A typical procedure is as follows. 20.0 g of Fmoc-Pro-Lac-OH.DCHA (equivalent to 34.02 mmol) was partitioned between 300 ml of ethyl acetate and 500 ml of 10% aqueous citric acid. The organic phase was then washed sequentially with the following aqueous solutions: 200 ml 10% citric acid and 200 ml of brine. The solution was then dried with anhydrous sodium sulphate and finally filtered and evaporated to yield a clear gum. This was dissolved in 1008 ml of dimethylformamide together with hydroxybenzotriazole (9.135 g, equivalent to 67.4 mmol) and 7.56 g DCC (36.5 mmol) and 150 µl of the solution dispensed into each well of 63 reaction trays. Pins were immersed into the solution for 16 h in sealed bags at 20° C. After coupling, the pins were washed for 15 min with methanol and air dried. Any unreacted amine groups on the pin were capped by acetylation with acetic anhydride. After washing, the pins were dried and stored until required. In this way, 6048 pins were coupled. It will be appreciated that the coupling the Fmoc-Pro-Lac-OH moeity to the pin uses the standard chemistry of solid phase peptide synthesis.

Using the usual Fmoc-chemistry steps, α-Boc lysine (ε-Fmoc) is coupled to the pins. In the example being cited, Fmoc-β alanine was then coupled to the growing peptide to act as a spacer entity between the desired peptide and the large diketopiperazine group of the cleaved peptide. The remaining amino acids of the sequence were then coupled to the growing peptide using the usual Fmoc-chemistry methods of peptide synthesis. The peptides were side-chain deprotected with trifluoroacetic acid:phenol:ethandithiol (95:2.5:2.5 v/w/v) for 6 h at room temperature. The pins were then air dried for 15 mins. They were then sonicated in 0.1% HCl in methanol/water (1:1) for 15 mins and then washed in pH 3 citrate-phosphate buffer for 5 h. The peptides were cleaved by immersing them into pH 7, 0.1M phosphate buffer (150 µl per well) for 16 h with gentle agitation under a nitrogen atmosphere at room temperature.

Figure 7A:
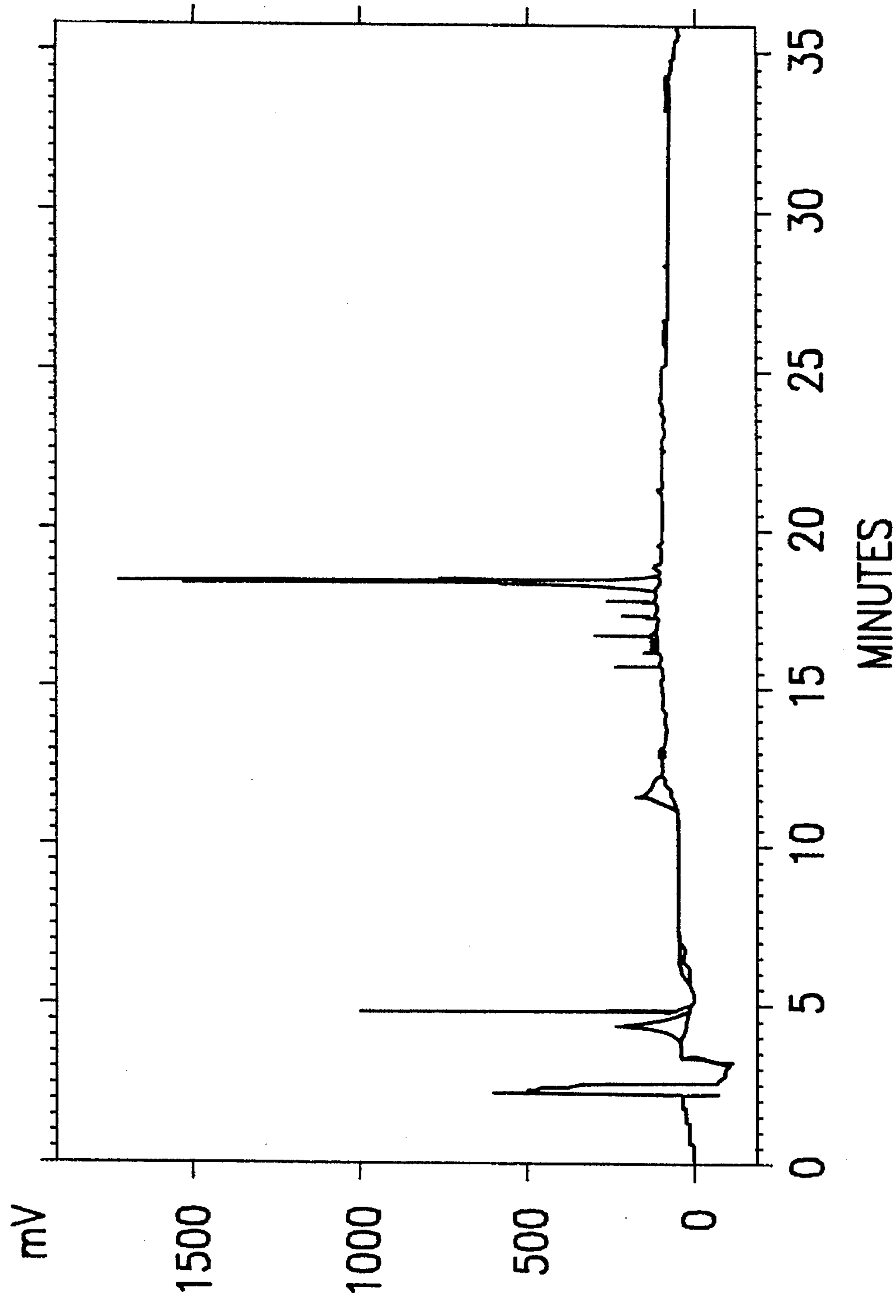
FIGS. 7(*a*) and 7(*b*) provide the HPLC tracing and mass spectrum, respectively of the peptide Ac-VQAAIDYING-β-cyclo(KP).
Figure 7B:
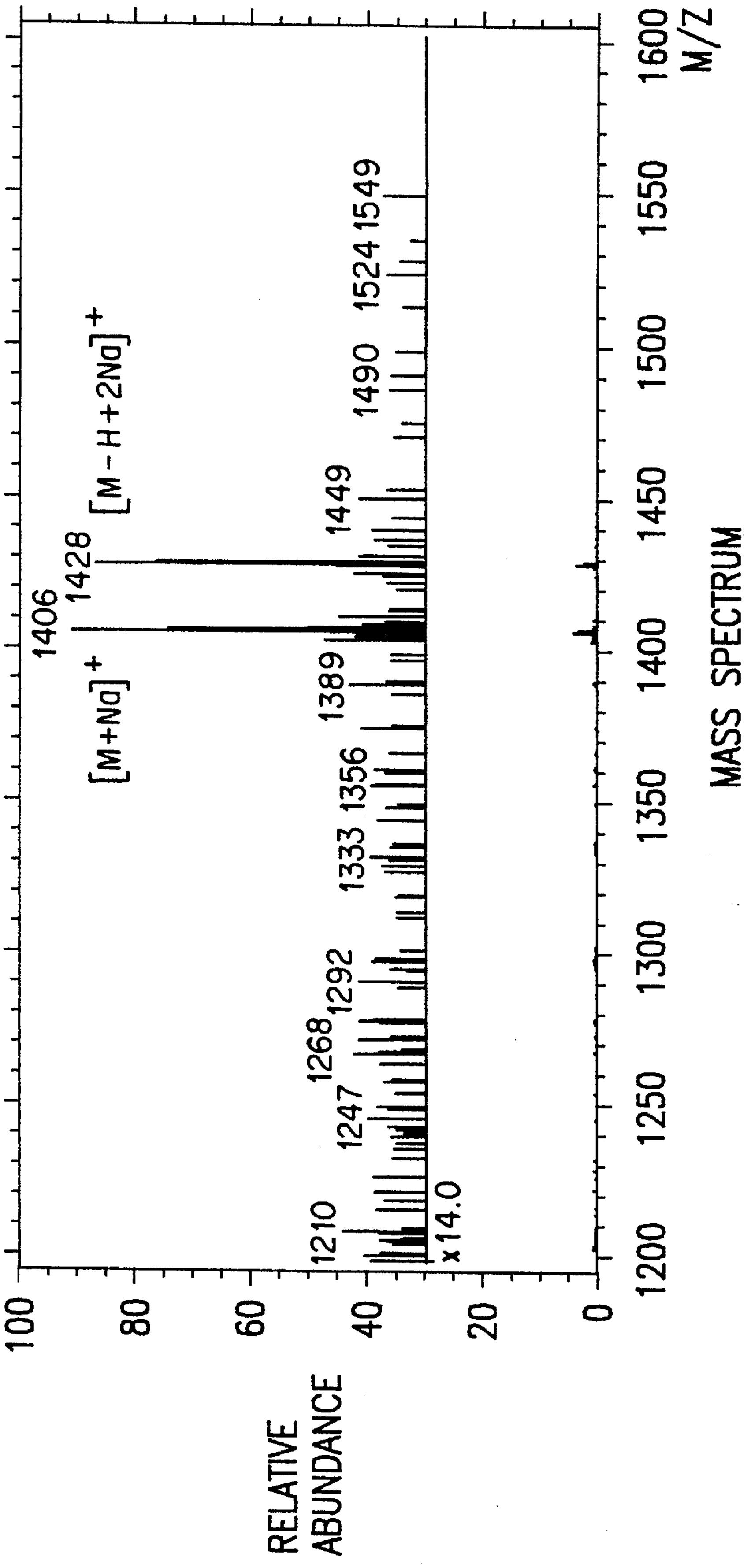

FIGS. 7*a* and 7*b* show the HPLC analysis of the peptide solution and demonstrates that the test peptide, one which is notoriously difficult to synthesize, was prepared with better than 90% purity. This figure also shows the mass spectrograph of the peptide solution and shows that the desired peptide was indeed synthesised. The cleaved peptide solutions from the hydrolysate of a single pin were also subjected to amino acid analysis and yielded the typical result shown in Table 2.

TABLE 2

AMINO ACID ANALYSIS OF Ac-VQAAIDYING-β-cyclo (KP)

| Amino acid | RELATIVE Found | MOLAR RATIO Expected |
|---|---|---|
| Aspartic acid (D) | 1.62 | 2 |
| Glutamic acid (E) | 0.78 | 1 |
| Glycine (G) | 0.52 | 1 |
| β-alanine (β) | 1.41 | 1 |
| Alanine (A) | 2.08 | 2 |
| Proline (P) | 1.37 | 1 |
| Tyrosine (Y) | 1.14 | 1 |
| Valine (V) | 1.02 | 1 |
| Isoleucine (I) | 2.22 | 2 |
| Lysine (K) | 0.83 | 1 |

This example illustrates that implementation of the invention yields the anticipated peptide with excellent purity, and also that reagents which simplify the routine synthesis of many different peptides can easily made. Similar results (with appropriate modifications to the weights of the reagent to account for the different molecular weights) have been obtained replacing lactic acid with glycolic acid and p-(hydroxymethyl) benzoic acid in forming the labile ester link.

EXAMPLE 5

Every overlapping decapeptide which could be made from the sequence of the β-chain of human choriogonadotrophin (hCG) were synthesised using serine as the ester link as described in Example 3. The sequence of hCG is:

| | | | | |
|---|---|---|---|---|
| 1 | SKEPLRPRCR | PINATLAVEK | EGCPVCITVN | TTICAGYCPT |
| 41 | MTRVLQGVLP | ALPQVVCNYR | DVRFESIRLP | GCPRGVNPVV |
| 81 | SYAVALSCQC | ALCRRSTTDC | GGPKDHPLTC | DDPRFQDSSS |
| 121 | SKAPPPSLPS | PSRLPGPSDT | PILPQ | |

80 ml of concentrated tetanus toxoid (1190 Lf/ml and protein concentration of 8.74 mg/ml) was dialyzed against pH 6.66 0.1M phosphate buffer. 222 mg of 6-maleimido caproic acid N-hydroxysuccinimide ester (MCS) was dissolved in 6 ml of dimethylformamide (DMF). To the dialyzed tetanus toxoid solution was added, with continuous stirring at room temperature, 1.5 ml of the MCS solution. 15 mins later a further 1.5 ml of this solution was added. 15 mins later again, the remaining MCS solution was added. Stirring continued for a further hour. The resulting solution was then dialyzed overnight against pH 7.2, 0.1M phosphate buffer to which sodium ethylene-diamine-tetra-acetic acid (EDTA) to a final concentration of 10 mM had been added. This resulting solution was diluted to 47% of its original strength with pH 7.2, 0.1M phosphate buffer to give a final concentration of MCS groups of 1.083 μmol/ml. Peptides were cleaved from the pins with 150 μl/pin of this solution and directly coupled to MCS-activated tetanus toxoid.

Mice were then vaccinated with the peptide/tetanus toxoid preparations. The peptide preparations were emulsified in Complete Freund's Adjuvant and were each injected by the intraperitoneal route into pairs of mice. A booster dose of the appropriate peptide preparation in Incomplete Freund's Adjuvant was given 17 days later. Blood samples were taken 21 days after the second inoculation.

Figure 8A:
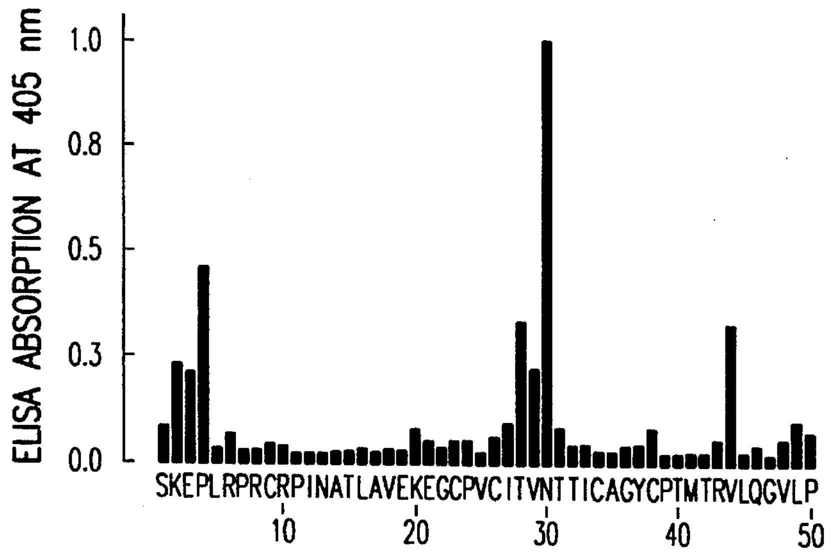
FIGS. 8(*a*), 8(*b*) and 8(*c*) illustrate the ability of antibodies raised against each possible dedapeptide corresponding to human choriogonadotropin to subsequently recognize the decapeptides as determined by ELISA.
Figure 8B:
Figure 8C:
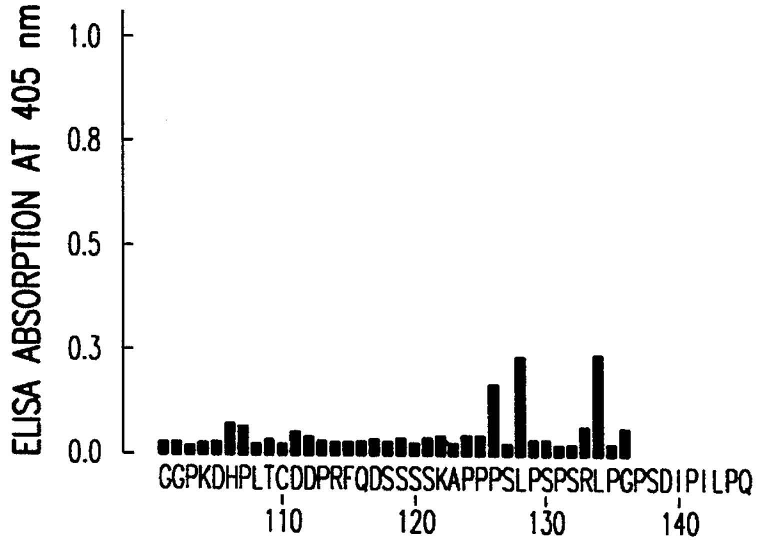

FIGS. 8*a*–8*c* show the result of testing the blood sample against the peptide with which the mice were vaccinated. The sera were diluted 1/100000 for testing. Thus, sample 30 is a pool of the sera from the two mice which had been vaccinated with the peptide NTTICAGYCP coupled to tetanus toxoid, and was found to react very strongly with the peptide NTTICAGYCP.

This illustrates the use of the invention in determining regions of a sequence which become potential candidates for a synthetic peptide vaccine.

EXAMPLE 6

This example provides illustrations of the use of the invention to give cleavable peptides without the need to have the diketopiperazine group at the carboxy terminal of the peptide.

Figure 9A:
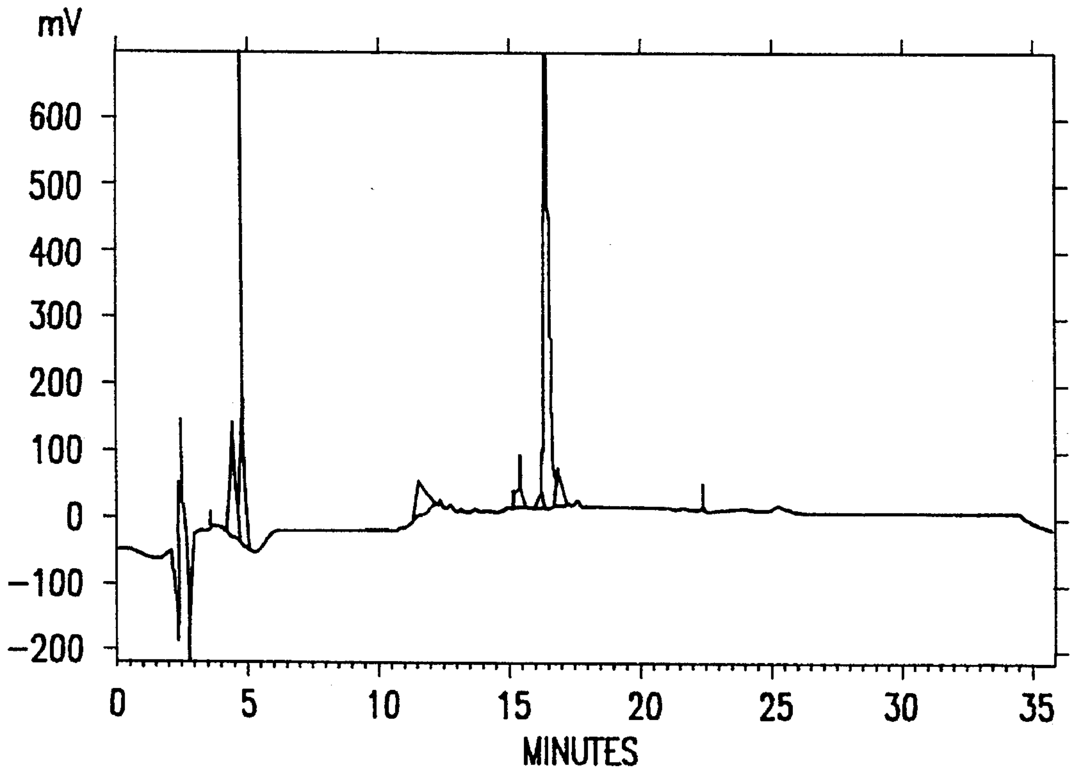
FIG. 9(*a*) illustrates the HLPC trace of a mixture resulting from NaOH induced cleavage of the peptide PGPSDTPILP from pins bearing an epsilon-Lys-Ala-Glycolate linker.

Fmoc-β Ala-Glyc-OH:DHCA was prepared using the method described in Example 4 except that glycolic acid replaced lactic acid and Fmoc-β alanine replaced Fmoc-proline. Weights were adjusted to take account of the different molecular weights. This compound was coupled to the pins as described in Example 4. The peptide PGPSDTPILP was synthesized on the pin and its side-chains deprotected as described earlier. The peptide was cleaved from the pin with 150 μl of 0.3% NaOH solution for 2.5 h at room temperature. After cleavage, the solution was neutralized with HCl. FIG. 9*a* is the HPLC analysis of this solution and demonstrates that the peptide was synthesized with excellent purity.

Figure 9B:
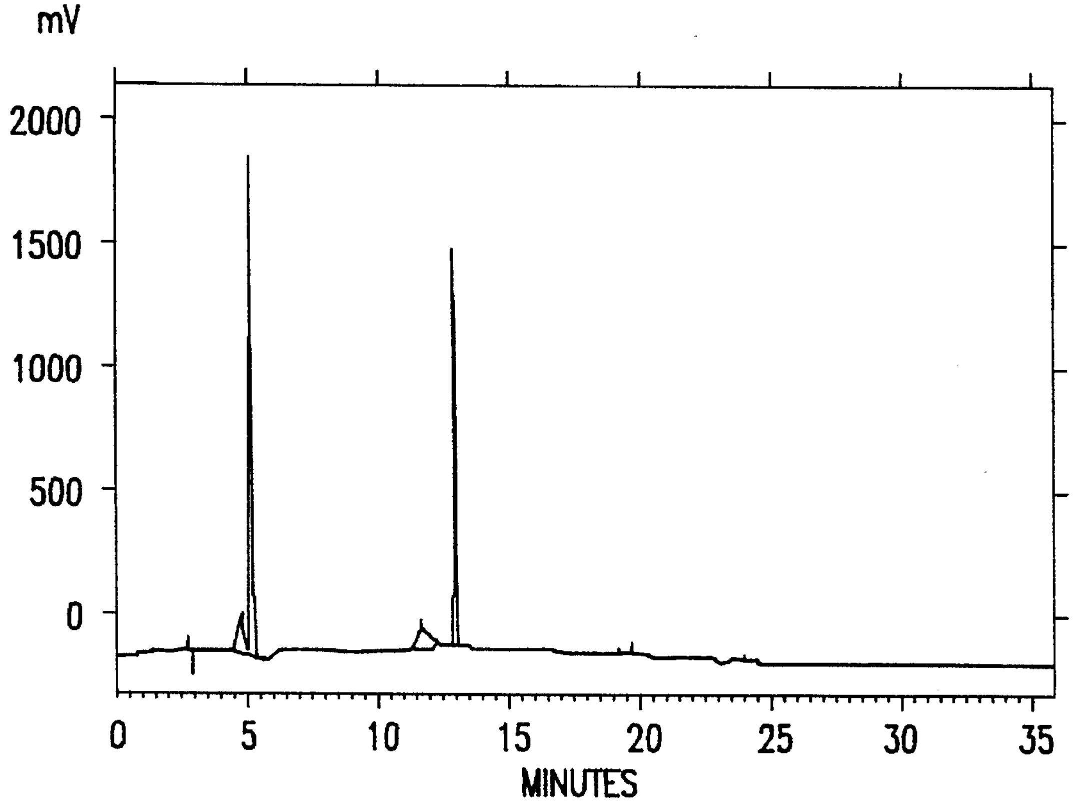

In a similar manner, the chromophore DNP and β-alanine were coupled to Fmoc-Pro-Lac-pins prepared as described in Example 4. This was cleaved from the pin by reaction with 150 μl of a 50:50 mixture of saturated methylamine in ethanol and water at room temperature for 2.5 hrs to yield DNP-β Ala-Pro-NH—$CH_3$. The solution was evaporated to dryness to remove excess methylamine. FIG. 9*b* is the HPLC analysis of the cleavage product and again demonstrates that it is of excellent purity.

Those skilled in the art will appreciate that the invention described herein is susceptible to variations and modifications other than those specifically described. It is to be understood that the invention includes all such variations and modifications which fall within its spirit and scope. The invention also includes all the steps, features, compositions and compounds referred to or indicated in this specification, individually or collectively, and any and all combinations of any two or more of said steps or features.

I claim:

1. A compound of the formula:

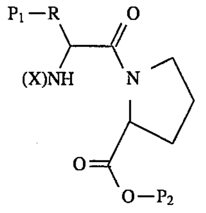

wherein (X) is a solid-phase peptide synthesis stable protecting group; R is an amino acid side chain having a functional group; and one of $P_1$ and $P_2$ is a peptide, and the other is a solid support with or without a spacer.

2. The compound of claim 1, wherein $P_2$ is a solid support.

3. The compound of claim 2, wherein said formula is:

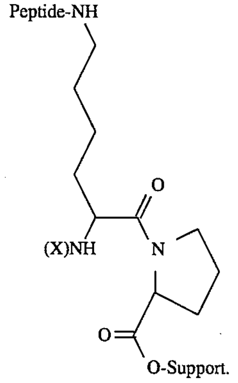

4. The compound of claim 1, wherein said formula is:

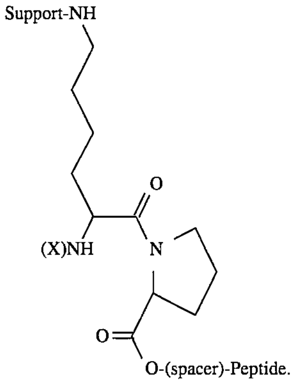

5. The compound of claim 1, wherein said spacer is $CH_2CH_2NH$.

6. A compound of the formula:

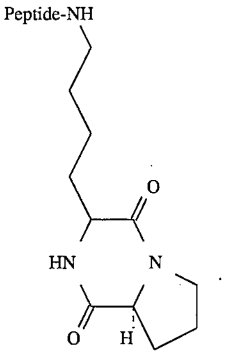

7. A method for preparing a derivatized peptide, said method comprising:

(i) providing a support of the formula:

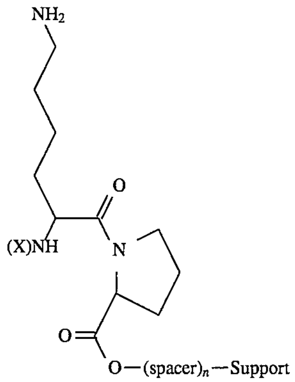

wherein (X) is a solid-phase peptide synthesis stable protecting group, and n is 0 or 1;

(ii) coupling a protected amino acid to the free $NH_2$ to provide a protected oligopeptide;

(iii) deprotecting the protected oligopeptide to provide a new free $NH_2$;

(iv) coupling a protected amino acid to the new free $NH_2$ to provide a new protected oligopeptide;

(v) repeating steps (iii) and (iv) until the desired peptide sequence is obtained;

(vi) removing (X) to provide a deprotected amine; and (vii) treating said deprotected amine with a mild base to yield a diketopiperazine terminus.

8. The method of claim 7, wherein said spacer is selected from the group consisting of N-acetyl serine, glycolic acid, lactic acid, and p-(hydroxymethyl) benzoic acid.

9. A method for preparing a derivatized peptide, said method comprising:

(i) providing a support of the formula:

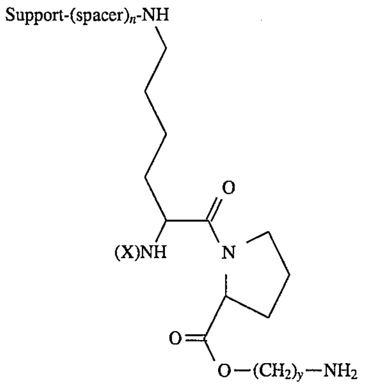

wherein (X) is a protecting group, n is 0 or 1, and y is 0 or an integer of from 2 to 6 inclusive;

(ii) coupling a protected amino acid to the free $NH_2$ to provide a protected oligopeptide;

(iii) deprotecting the protected oligopeptide to provide a new free $NH_2$;

(iv) coupling a protected amino acid to the new free $NH_2$ to provide a new protected oligopeptide;

(v) repeating steps (iii) and (iv) until the desired peptide sequence is obtained;

(vi) removing (X) to provide a deprotected amine; and (vii) treating said deprotected amine with a mild base to yield an $—NH—(CH_2)_y—OH$ terminus.

* * * * *